United States Patent [19]
Ferris

[11] Patent Number: 4,588,728
[45] Date of Patent: May 13, 1986

[54] TREATMENT OF DRUG INDUCED PSYCHOSIS

[75] Inventor: Robert M. Ferris, Cary, N.C.

[73] Assignee: Burroughs Wellcome Co., Research Triangle Park, N.C.

[21] Appl. No.: 716,752

[22] Filed: Mar. 27, 1985

[51] Int. Cl.[4] .......................................... A61K 31/495
[52] U.S. Cl. .................................................. 514/255
[58] Field of Search ........................................ 514/255

Primary Examiner—Stanley J. Friedman
Attorney, Agent, or Firm—Donald Brown

[57] ABSTRACT

It is now disclosed that cis-9[3-(3,5-dimethyl-piperazinyl)propyl]carbazole is useful in reversing the detrimental psychotic conditions induced in humans by phencyclidine (PCP) and/or sigma opioid agonists.

3 Claims, No Drawings

TREATMENT OF DRUG INDUCED PSYCHOSIS

TREATMENT OF DRUG INDUCED PSYCHOSIS

The illicit drug 1-(1-phenylcyclohexyl)piperdine (PCP), generically named phencyclidine, (frequently used in the form of an acid addition salt, e.g., hydrochloride salt) is a potent inducer of psychosis. In recent years the extent of the abuse of PCP has grown dramatically. Its over-dose now leads to an estimated 15,000 hospitalization per year. *Psychiatric News*, Sept. 7, 1984, reports, "PCP abusers are a serious problem for the community as well as for the hospital staff, because drug reactions often involve violent or bizarre behavior, such as grandiosity, with patients showing great difficulty in impulse control." Many patients with PCP associated psychosis fail to respond to antipsychotic drugs now in clinical use. Moreover, such drugs increase the likelihood of seizures and vascular instability (*Bio. Ther. in Psy*, 34).

It has now been found that cis-9[3-(3,5-dimethyl-piperazinyl)propyl]carbazole, disclosed as the compound of formula (I) in U.S. Pat. No. 4,379,160 (issued Apr. 5, 1983), which is incorporated herein by reference, is effective in inhibiting the binding of phencyclidine and sigma opioid agonists (For sigma opioid agonists see *J. Pharmacol. Exp. Ther.* 197: 518–532, 1976) to phencyclidine and sigma receptors present in rat and/or guinea pig brain. The $IC_{50}$ for compound (I) to inhibit $^3$H-phencyclidine binding to phencyclidine receptors is $4.5 \times 10^{-5}$M and its $IC_{50}$ for inhibiting $^3$H-(+)-SKF 10,047 binding to sigma receptors is $5.0 \times 10^{-7}$M. Compound of formula (I) or a pharmaceutically acceptable salt thereof is effective in reversing the deterimental psychotic conditions in human patients suffering from the effects of phencyclidine and/or sigma opioid agonists such as N-allylnormetazocine, pentazocine, cyclazocine, etc. The compound of formula (I) (hereinafter referred to as "compond I" or "the active ingredient") or a pharmaceutically acceptable acid addition salt thereof, e.g., hydrochloride, methansulfonate, etc.) is also effective in reversing the psychosis and other effects induced by endogenous agonists of both the phencyclidine and sigma receptors; and can, therefore, be considered as a therapeutic agent useful in treating the disastrous effects of agonists (endogenous or synthetic) of the phencyclidine and/or sigma receptors, e.g. phencyclidine, pentazocine, cyclazocine, N-allylnormetazacine, etc.

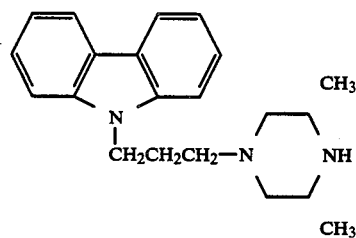

(I)

The compound I (the active ingredient) or the pharmaceutically acceptable acid addition salt thereof is preferably administered in unit dosage form to the human patient being treated, who has been identified as suffering from psychosis induced by PCP or an acid addition salt thereof or a sigma receptor agonist or having taken an amount of one of these agents which would likely induce psychosis. The active ingredient or pharmaceutically acceptable salt thereof (preferably as the hydrochloride) may be presented as an oral unit preparation (for example as a cachet, tablet or capsule) containing one or more pharmaceutically acceptable carriers which may be in the form of solid diluents such as lactose, cornstarch, micronized silica gel as well as other excipients known in the art. However, for the type of treatment being considered herein the patient may be irrational, violent, or, in some cases, unconscious, and oral administration may not be feasible, and compound I must be given by injection.

While the overall dosage range is within that disclosed in U.S. Pat. No. 4,379,160, the amount of the unit dose and the interval may vary considerably from that previously disclosed and even from case to case. Of course the attending medical practitioner must determine the unit dose and dosing interval, but situations requiring such a therapeutic agent dictate that a substantial level of compound I be reached in the patient as rapidly as possible. Therefore, the initial dose in the form of an injection would be in the range of 5.0 mg/kg to 15.0 mg/kg. It is also possible that iv administration over a period of hours might be indicated. The amount and timing of subsequent treatment would be based on the patients rate of recovery.

EXAMPLE 1

The dihydrochloride salt of the compound of formula I is administered as an injection to a 70 kg human who has been identified by a medical practitioner as suffering from phencyclidine induced psychosis. The initial injection for such a human is 200 mg and is followed with injections of 100 mg at 2 hour intervals thereafter until the symptoms of psychosis disappear. The patient is then treated at the rate of 100 mg at 4 hour intervals for the next 48 hours. Treatment may be extended at the discretion of the attending medical practitioner.

EXAMPLE 2

The procedure of Example 1 is followed, however, the methansulfonate salt of compound I is used.

I claim:

1. A method of treating a human patient identified as suffering from psychosis induced by phencyclidine (or an acid addition salt thereof) or identified as having taken a psychosis inducing amount of phencyclidine (or an acid addition salt thereof) comprising the administration to said patient of an effective phencyclidine induced psychosis reversing amount of the compound of formula (I) or a pharmaceutically acceptable salt thereof

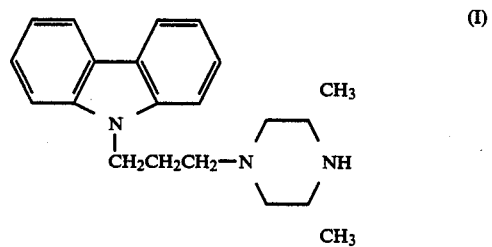

(I)

2. The method of claim 1 in which a pharmaceutically acceptable salt of the compound of formula (I) is used.

3. The method of claim 2 in which the dihydrochloride salt is used.

* * * * *